(12) United States Patent
Williams et al.

(10) Patent No.: US 12,135,146 B2
(45) Date of Patent: Nov. 5, 2024

(54) AIR CONDITIONER UNIT OR STERILIZATION LIGHT ASSEMBLY AND METHODS OF OPERATION

(71) Applicant: Haier US Appliance Solutions, Inc., Wilmington, DE (US)

(72) Inventors: Craig Benjamin Williams, Louisville, KY (US); Timothy Scott Shaffer, La Grange, KY (US)

(73) Assignee: Haier US Appliance Solutions, Inc., Wilmington, DE (US)

( * ) Notice: Subject to any disclaimer, the term of this patent is extended or adjusted under 35 U.S.C. 154(b) by 533 days.

(21) Appl. No.: 17/382,702

(22) Filed: Jul. 22, 2021

(65) Prior Publication Data

US 2023/0028978 A1   Jan. 26, 2023

(51) Int. Cl.
*F24F 8/22* (2021.01)
*A61L 9/20* (2006.01)
(Continued)

(52) U.S. Cl.
CPC ............... *F24F 8/22* (2021.01); *A61L 9/20* (2013.01); *F24F 1/0328* (2019.02); *F24F 11/00* (2013.01);
(Continued)

(58) Field of Classification Search
CPC .......... F24F 8/22; F24F 11/00; F24F 2140/50; F24F 1/0328; F24F 11/77; A61L 9/20;
(Continued)

(56) References Cited

U.S. PATENT DOCUMENTS 5,755,103 A * 5/1998 Na .................. F24F 1/0076
62/264
5,891,399 A * 4/1999 Owesen ............ A61L 9/20
422/121

(Continued)

FOREIGN PATENT DOCUMENTS

CN        1712825 A  * 12/2005  ............... A61L 9/16
CN      107355854 A  * 11/2017
(Continued)

*Primary Examiner* — Edelmira Bosques
*Assistant Examiner* — Frances F. Hamilton
(74) *Attorney, Agent, or Firm* — Dority & Manning, P.A.

(57) ABSTRACT

An air conditioner unit may include a housing, an outdoor heat exchanger, an indoor heat exchanger, a compressor, a sterilization light assembly, and a controller. The housing may define an indoor portion and an outdoor portion. The housing may further define an exhaust outlet downstream from the indoor portion to exhaust air therefrom. The sterilization light assembly may be disposed within the indoor portion. The controller may be in operable communication with the indoor fan and the sterilization light assembly. The controller may be configured to initiate a sterilizing operation. The sterilizing operation may include directing activation of the indoor fan to motivate air through the indoor portion, detecting activation of the indoor fan to motivate air through the indoor portion, and directing activation of the sterilization light assembly to transmit an ultraviolet light emission within the indoor portion based on detected activation of the indoor fan.

13 Claims, 9 Drawing Sheets

(51) Int. Cl.
*F24F 1/0328* (2019.01)
*F24F 11/00* (2018.01)
*F24F 140/50* (2018.01)

(52) U.S. Cl.
CPC ...... *A61L 2209/111* (2013.01); *A61L 2209/12* (2013.01); *A61L 2209/16* (2013.01); *F24F 2140/50* (2018.01)

(58) Field of Classification Search
CPC ........... A61L 2209/111; A61L 2209/12; A61L 2209/16
USPC .......................................................... 454/229
See application file for complete search history.

(56) References Cited

U.S. PATENT DOCUMENTS

| | | | | |
|---|---|---|---|---|
| 6,438,971 | B1* | 8/2002 | Lentz | F24F 8/192 |
| | | | | 62/264 |
| 6,673,137 | B1* | 1/2004 | Wen | A61L 9/14 |
| | | | | 422/124 |
| 7,632,459 | B2 | 12/2009 | Hammer | |
| 2003/0021720 | A1* | 1/2003 | Reisfeld | B01D 53/8668 |
| | | | | 422/4 |
| 2007/0181000 | A1* | 8/2007 | Wilson | F24F 11/77 |
| | | | | 96/134 |
| 2007/0275651 | A1* | 11/2007 | Palmer | F24F 8/192 |
| | | | | 454/238 |
| 2010/0256821 | A1* | 10/2010 | Jeung | G05B 15/02 |
| | | | | 318/504 |
| 2011/0033346 | A1* | 2/2011 | Bohlen | F24F 8/80 |
| | | | | 422/186.3 |
| 2013/0052090 | A1* | 2/2013 | Bohlen | B01D 53/885 |
| | | | | 422/121 |
| 2017/0333587 | A1* | 11/2017 | Bender | B01D 46/0027 |
| 2019/0063763 | A1* | 2/2019 | Kleinberger | B01D 46/521 |
| 2022/0221167 | A1* | 7/2022 | Blackwood | F24F 3/16 |

FOREIGN PATENT DOCUMENTS

| | | | | |
|---|---|---|---|---|
| CN | 209926487 | U | | 1/2020 |
| CN | 110848943 | A * | | 2/2020 |
| CN | 111336664 | A * | | 6/2020 |
| CN | 111623422 | A * | | 9/2020 |
| CN | 111637605 | A | | 9/2020 |
| CN | 112539463 | A * | | 3/2021 |
| CN | 111473485 | B * | 5/2021 | ............... A61L 9/20 |
| DE | 102020120281 | A1 * | 6/2021 | ........... A22B 5/0076 |
| KR | 101796291 | B1 | 11/2017 | |
| KR | 20180010747 | A * | 1/2018 | ............. F24F 11/30 |

* cited by examiner

AIR CONDITIONER UNIT OR STERILIZATION LIGHT ASSEMBLY AND METHODS OF OPERATION

FIELD OF THE INVENTION

The present subject matter relates generally to air conditioner units and more particularly to an air conditioner unit having a sterilization light assembly for sterilizing air within the air conditioner unit.

BACKGROUND OF THE INVENTION

Air conditioner or conditioning units are conventionally used to adjust the temperature indoors (i.e., within structures such as dwellings and office buildings). For example, a packaged terminal air conditioners (PTAC) may be used to adjust the temperature in, for example, a single room or group of rooms of a structure. A PTAC unit includes an indoor portion and an outdoor portion. The indoor portion generally communicates (e.g., exchanges air) with the room/group of rooms within a building, and the outdoor portion generally communicates (e.g., exchanges air) with the area outside the building. Accordingly, the air conditioner unit generally extends through, for example, a wall of the structure. Generally, a fan may be operable to rotate to motivate air through the indoor portion. Another fan may be operable to rotate to motivate air through the outdoor portion. A sealed cooling system including a compressor is generally housed within the air conditioner unit to treat (e.g., cool or heat) air as it is circulated through, for example, the indoor portion of the air conditioner unit.

One issue that may arise during the use of a conventional air conditioner unit (e.g., PTAC) is the presence of potentially damaging microbes, bacteria, or viruses within the surrounding air. In particular, the such microbes, bacteria, or viruses may be circulated or propelled through a room as an air conditioner unit draws in and expels air. This may, in turn, make it difficult to prevent transmission of such microbes, bacteria, or viruses to individuals located within the same room.

Although some attempts have been made to use the sterilization properties of ultraviolet (UV) light to help reduce or eliminate microbes, bacteria, or viruses; these attempts may have a number of drawbacks. For instance, it can be difficult to direct light to a significant portion of air flowing through an air conditioner unit without requiring a light assembly that is especially bulky or energy intensive. Additionally or alternatively, it may be difficult to mount a light assembly in such a way that it can reliably sterilize air while preventing damage that might occur to the light assembly (e.g., from moisture or excessive heat generated within an air conditioner unit). Separate from or in addition to mounting concerns, it may be difficult to reliably operate the unit, including the lighting assembly. Complex control schemes may reduce reliability, increase cost of development/assembly/maintenance, or otherwise degrade a user's experience. What's more, most existing attempts at using UV light have required installation of a UV light source within an air conditioner unit during assembly of the unit itself. This has been it virtually impossible for consumers to make use of UV sterilization with existing or previously purchased air conditioner units that were not originally assembled with a UV light source.

As a result, an air conditioner unit, light assembly, or methods of operating the same that address one or more of the above issues would be useful. In particular, it may be advantageous to provide an air conditioner unit, assembly, or methods having features for effectively or reliably sterilizing air flowing therethrough (e.g., without significant increases to system size, cost to manufacture or operate, etc.). Additionally or alternatively, an assembly (or methods of operation), such as a kit, for using UV light sterilization that can be readily incorporated into an existing or previously assembled air conditioner unit (e.g., without requiring reprogramming of the unit) would be useful.

BRIEF DESCRIPTION OF THE INVENTION

Aspects and advantages of the invention will be set forth in part in the following description, or may be obvious from the description, or may be learned through practice of the invention.

In one exemplary aspect of the present disclosure, a method of operating an air conditioner unit is provided. The method may include directing activation of an indoor fan to motivate air through an indoor portion of the air conditioner unit. The method may also include detecting activation of the indoor fan to motivate air through the indoor portion. The method may further include directing activation of a sterilization light assembly to transmit an ultraviolet light emission within the indoor portion based on detected activation of the indoor fan.

In another exemplary aspect of the present disclosure, an air conditioner unit is provided. The air conditioner unit may include a housing, an outdoor heat exchanger, an indoor heat exchanger, a compressor, a sterilization light assembly, and a controller. The housing may define an indoor portion and an outdoor portion. The housing may further define an exhaust outlet downstream from the indoor portion to exhaust air therefrom. The outdoor heat exchanger assembly may be disposed in the outdoor portion and include an outdoor heat exchanger. The indoor heat exchanger assembly may be disposed in the indoor portion and include an indoor heat exchanger and an indoor fan. The compressor may be in fluid communication with the outdoor heat exchanger and the indoor heat exchanger to circulate a refrigerant between the outdoor heat exchanger and the indoor heat exchanger. The sterilization light assembly may be disposed within the indoor portion. The controller may be in operable communication with the indoor fan and the sterilization light assembly. The controller may be configured to initiate a sterilizing operation. The sterilizing operation may include directing activation of the indoor fan to motivate air through the indoor portion, detecting activation of the indoor fan to motivate air through the indoor portion, and directing activation of the sterilization light assembly to transmit an ultraviolet light emission within the indoor portion based on detected activation of the indoor fan.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures.

DETAILED DESCRIPTION

Figure 1:
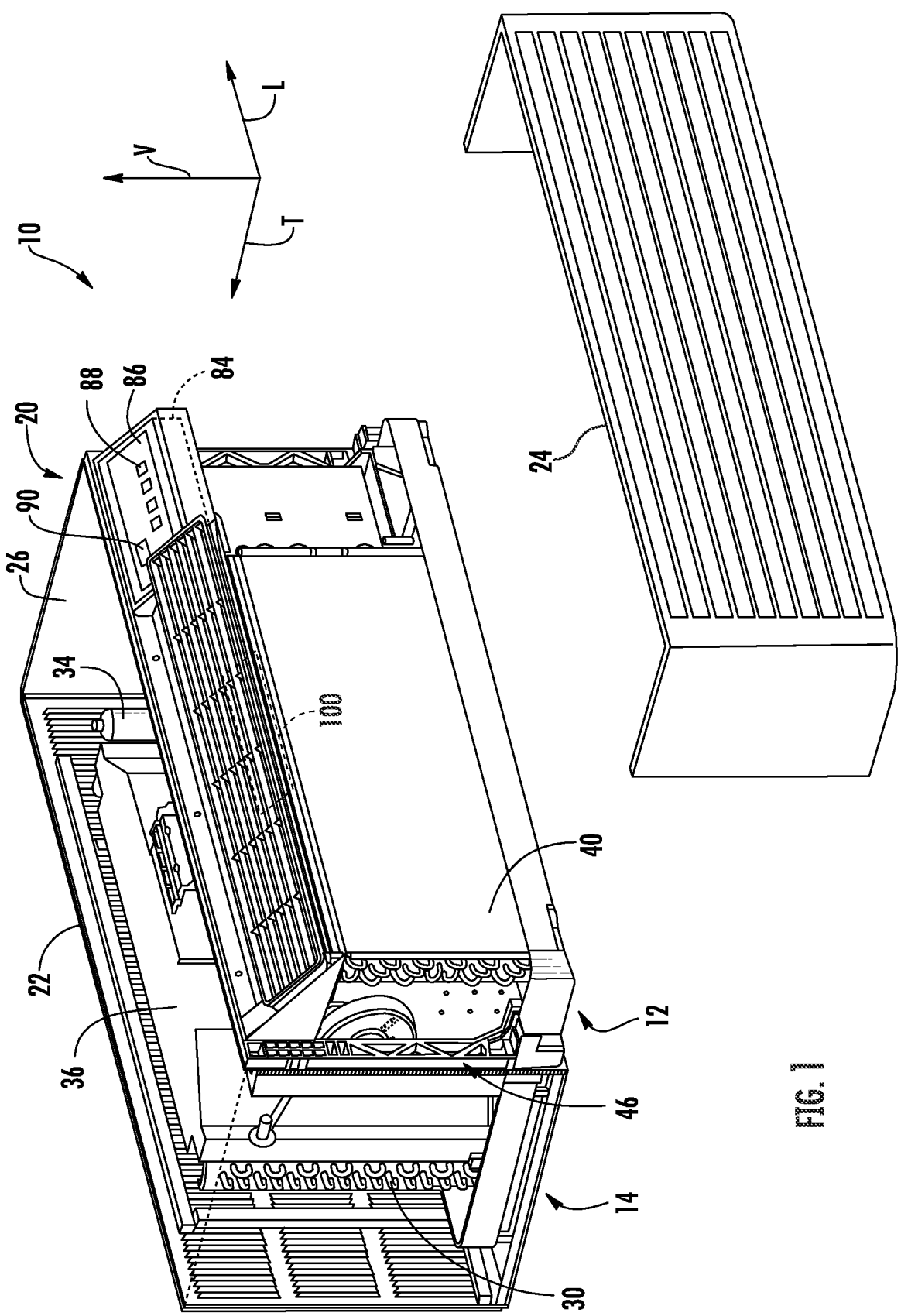
FIG. 1 provides a perspective view of an air conditioner unit, with part of an indoor portion exploded from a remainder of the air conditioner unit for illustrative purposes, according to exemplary embodiments of the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the term "or" is generally intended to be inclusive (i.e., "A or B" is intended to mean "A or B or both"). The terms "first," "second," and "third" may be used interchangeably to distinguish one component from another and are not intended to signify location or importance of the individual components. The terms "upstream" and "downstream" refer to the relative flow direction with respect to fluid flow (e.g., airflow or refrigerant flow) in a fluid pathway. For example, "upstream" refers to the flow direction from which the fluid flows, and "downstream" refers to the flow direction to which the fluid flows.

Referring now to FIG. 1, an air conditioner unit 10 is provided. The air conditioner unit 10 is a one-unit type air conditioner, also conventionally referred to as a packaged terminal air conditioner (PTAC) unit. The unit 10 includes an indoor portion 12 and an outdoor portion 14, and generally defines a vertical direction V, a lateral direction L, and a transverse direction T. Each direction V, L, T is perpendicular to each other, such that an orthogonal coordinate system is generally defined.

A housing 20 of the unit 10 may contain various other components of the unit 10. Housing 20 may include, for example, a rear grill 22 and a room front 24 which may be spaced apart along the transverse direction T by a wall sleeve 26. The rear grill 22 may be part of the outdoor portion 14, and the room front 24 may be part of the indoor portion 12. Components of the outdoor portion 14, such as an outdoor heat exchanger 30, outdoor fan 32, and compressor 34 may be housed within the wall sleeve 26. A casing 36 may additionally enclose the outdoor fan 32, as shown.

Although described in the context of a PTAC unit, an air conditioner unit as disclosed herein, may be provided as a saddle window air conditioner, single-package vertical unit (SPVU), vertical packaged air conditioner (VPAC), through-window air conditioner unit, or any other suitable air conditioner unit. The air conditioner 10 is intended only as an exemplary unit and does not otherwise limit the scope of the present disclosure. Thus, it is understood that the present disclosure may be equally applicable to other types of air-treatment units.

Figure 2:
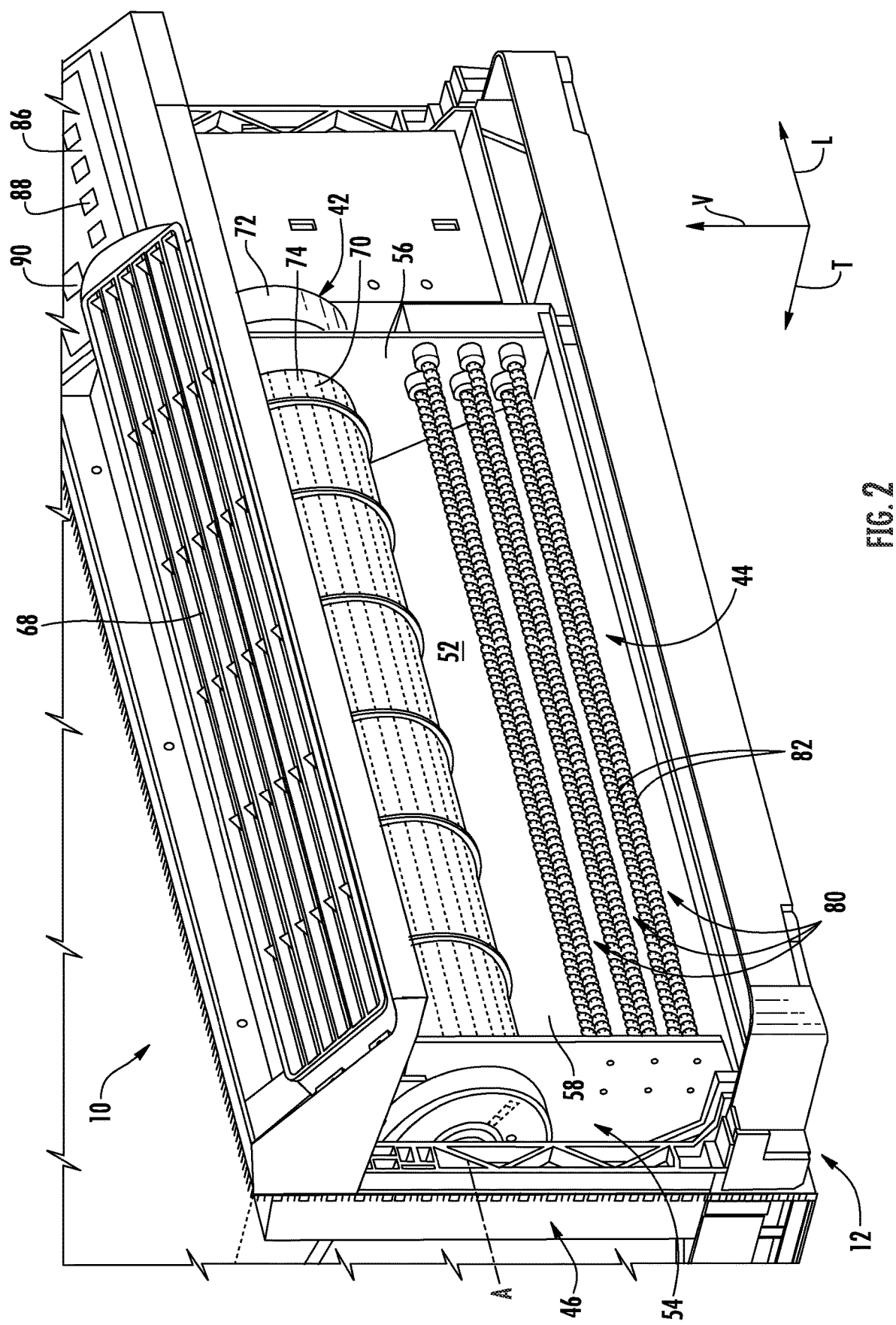
FIG. 2 provides a perspective view of components of an indoor portion of the exemplary air conditioner unit of FIG. 1.

Referring now also to FIG. 2, indoor portion 12 may include, for example, an indoor heat exchanger 40, an indoor or blower fan 42, and a heating unit 44. These components may, for example, be housed behind the room front 24 of housing 20. Additionally, a bulkhead 46 of housing 20 may generally support or house various other components or portions thereof of the indoor portion 12, such as the blower fan 42 and the heating unit 44. Bulkhead 46 may generally separate and define the indoor portion 12 and outdoor portion 14.

Figure 3:
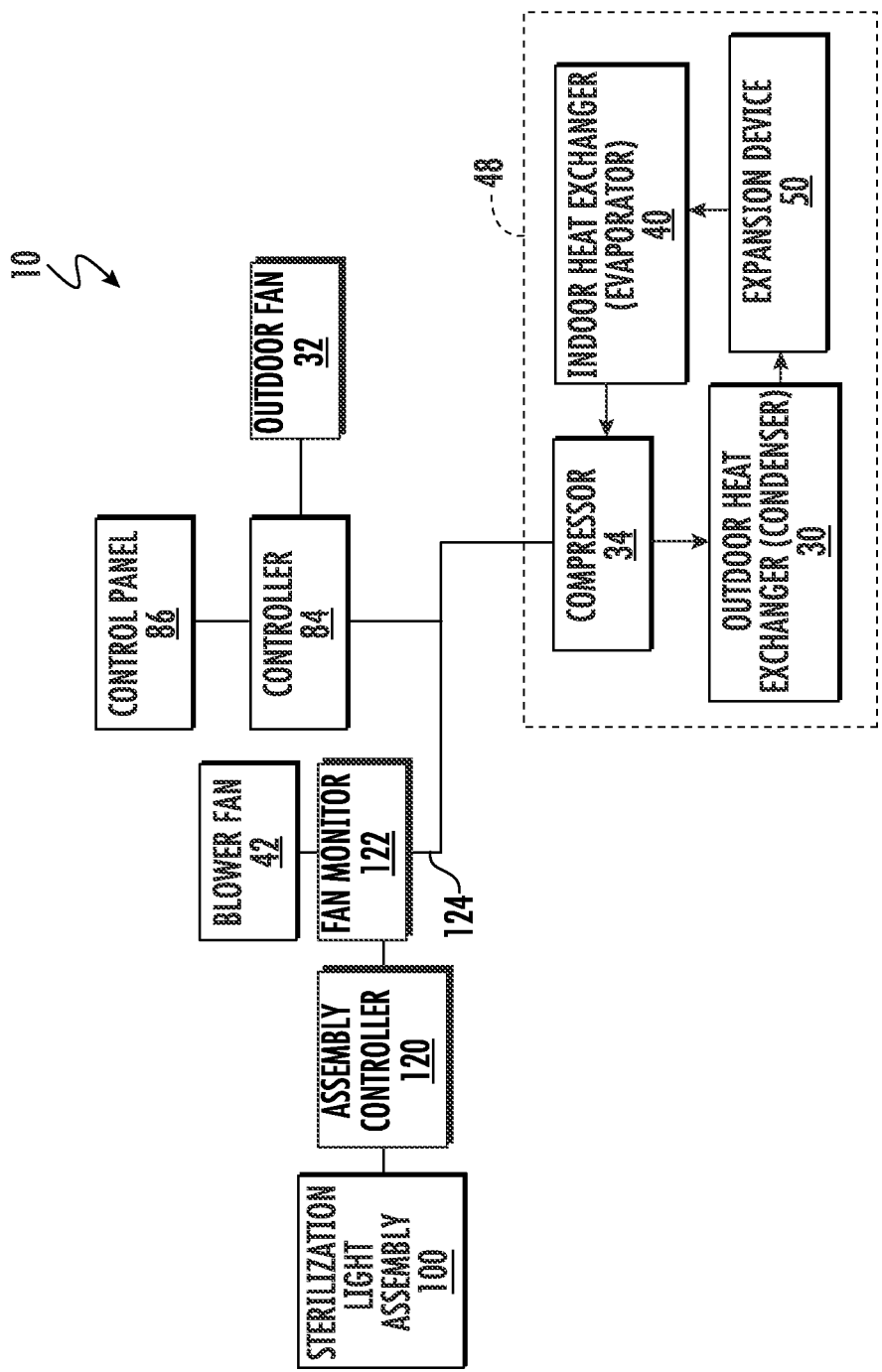
FIG. 3 provides a schematic view of a refrigeration loop in accordance with exemplary embodiments of the present disclosure.

Outdoor and indoor heat exchangers 30, 40 may be components of a refrigeration loop 48, which is shown schematically in FIG. 3. Refrigeration loop 48 may, for example, further include compressor 34 and an expansion device 50. As illustrated, compressor 34 and expansion device 50 may be in fluid communication with outdoor heat exchanger 30 and indoor heat exchanger 40 to flow refrigerant therethrough as is generally understood. More particularly, refrigeration loop 48 may include various lines for flowing refrigerant between the various components of refrigeration loop 48, thus providing the fluid communication there between. Refrigerant may thus flow through such lines from indoor heat exchanger 40 to compressor 34, from compressor 34 to outdoor heat exchanger 30, from outdoor heat exchanger 30 to expansion device 50, and from expansion device 50 to indoor heat exchanger 40. The refrigerant may generally undergo phase changes associated with a refrigeration cycle as it flows to and through these various components, as is generally understood. One suitable refrigerant for use in refrigeration loop 48 is 1,1,1,2-Tetrafluoroethane, also known as R-134A, although it should be understood that the present disclosure is not limited to such example and rather that any suitable refrigerant may be used.

As is understood, refrigeration loop 48 may be alternately operated as a refrigeration assembly (and thus perform a refrigeration cycle) or a heat pump (and thus perform a heat pump cycle). When refrigeration loop 48 is operating in a cooling mode and thus performs a refrigeration cycle, the indoor heat exchanger 40 acts as an evaporator and the outdoor heat exchanger 30 acts as a condenser. Alternatively, when the assembly is operating in a heating mode and thus performs a heat pump cycle, the indoor heat exchanger 40 acts as a condenser and the outdoor heat exchanger 30 acts as an evaporator. The outdoor and indoor heat exchangers 30, 40 may each include coils through which a refrigerant may flow for heat exchange purposes, as is generally understood.

In exemplary embodiments, expansion device 50 is disposed in the outdoor portion 14 between the indoor heat exchanger 40 and the outdoor heat exchanger 30. Optionally, expansion device 50 may be an electronic expansion valve that enables controlled expansion of refrigerant, as is generally understood. More specifically, electronic expansion device 50 may be configured to precisely control the expansion of the refrigerant to maintain, for example, a desired temperature differential of the refrigerant across the indoor heat exchanger 40. In other words, electronic expansion device 50 throttles the flow of refrigerant based on the reaction of the temperature differential across indoor heat exchanger 40 or the amount of superheat temperature differential, thereby ensuring that the refrigerant is in the gaseous state entering compressor 34. In alternative embodiments, expansion device 50 may be a capillary tube or another suitable expansion device configured for use in a thermodynamic cycle.

Figure 4:
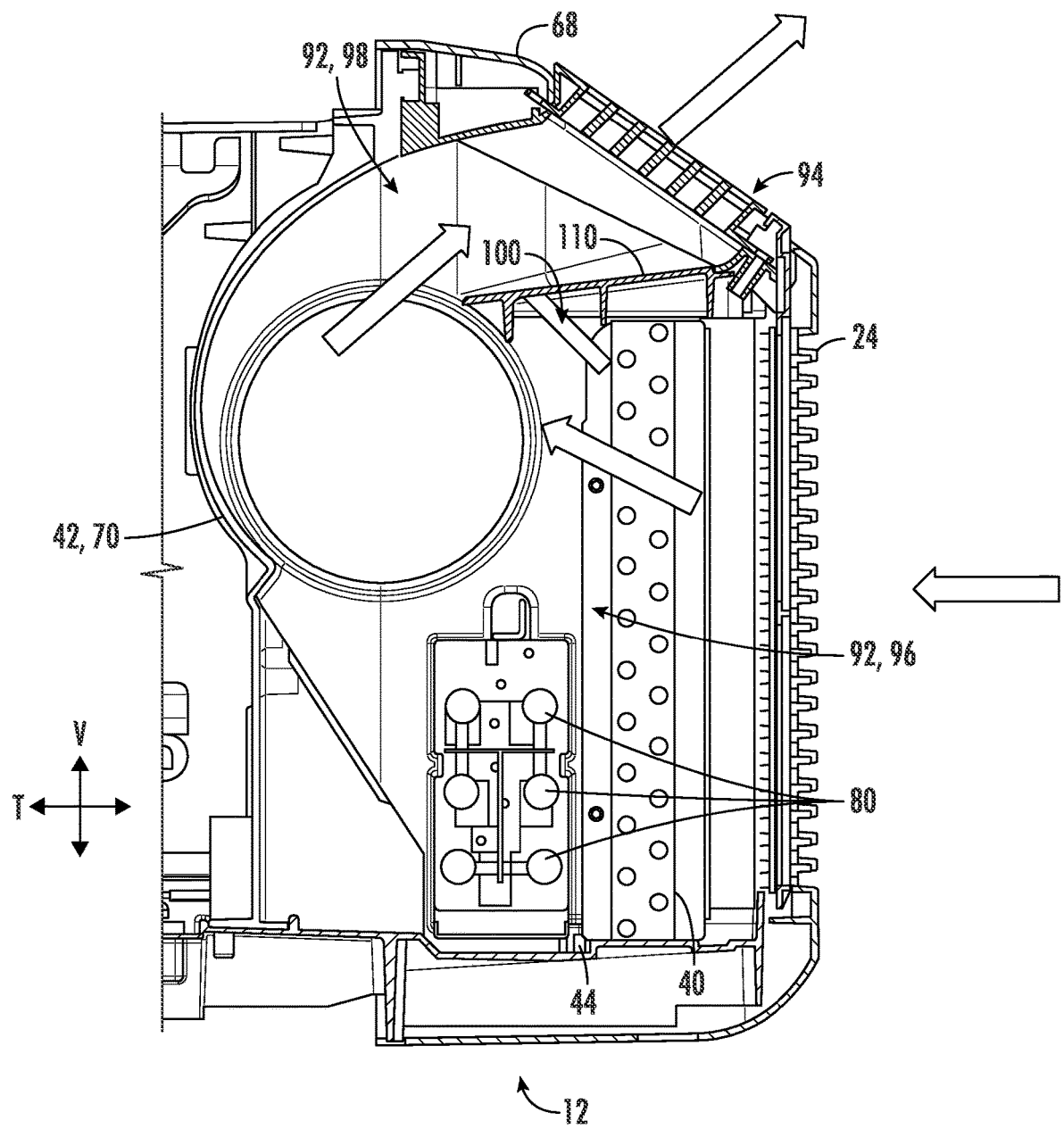
FIG. 4 provides a side sectional view of components of an indoor portion of the exemplary air conditioner unit of FIG. 1.
Figure 5:
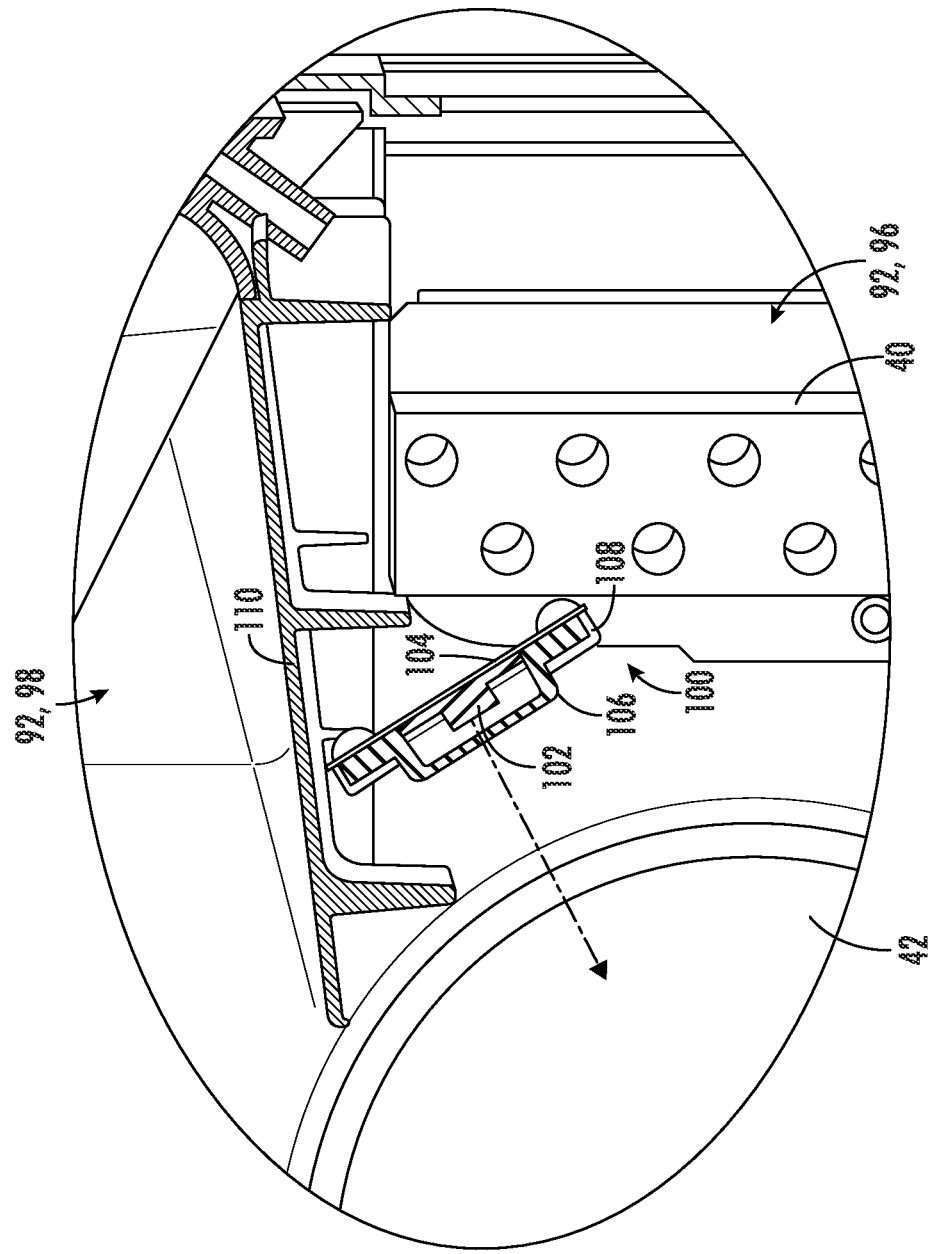
FIG. 5 provides a magnified side sectional view of components of the indoor portion of the exemplary air conditioner unit of FIG. 1.
Figure 6:
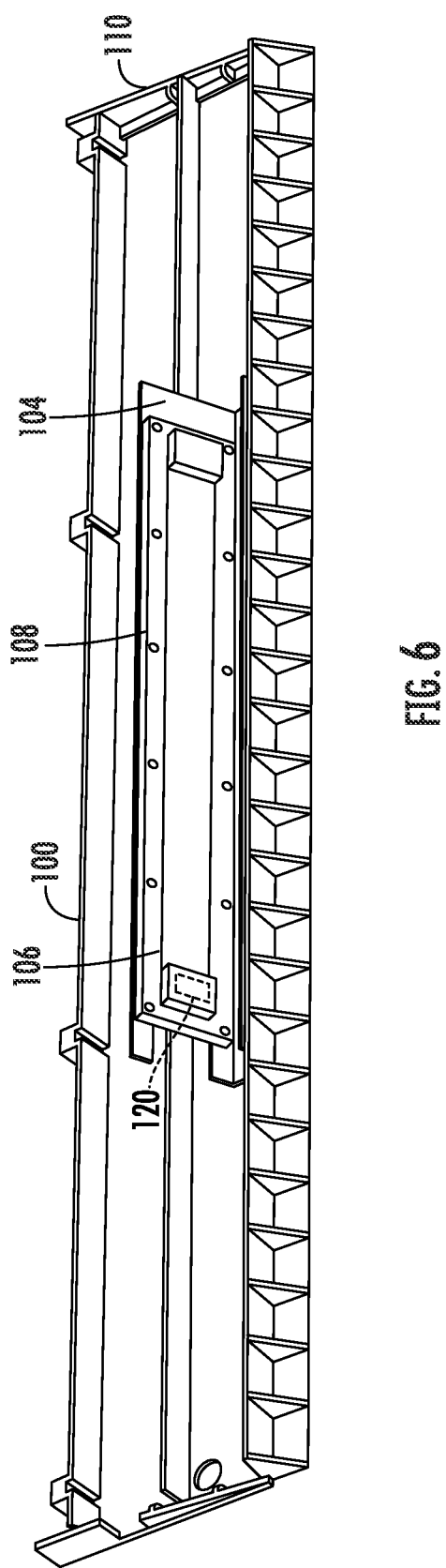
FIG. 6 provides a bottom perspective view of a cutoff panel and sterilization light assembly, in isolation, of the exemplary air conditioner unit of FIG. 1.
Figure 7:
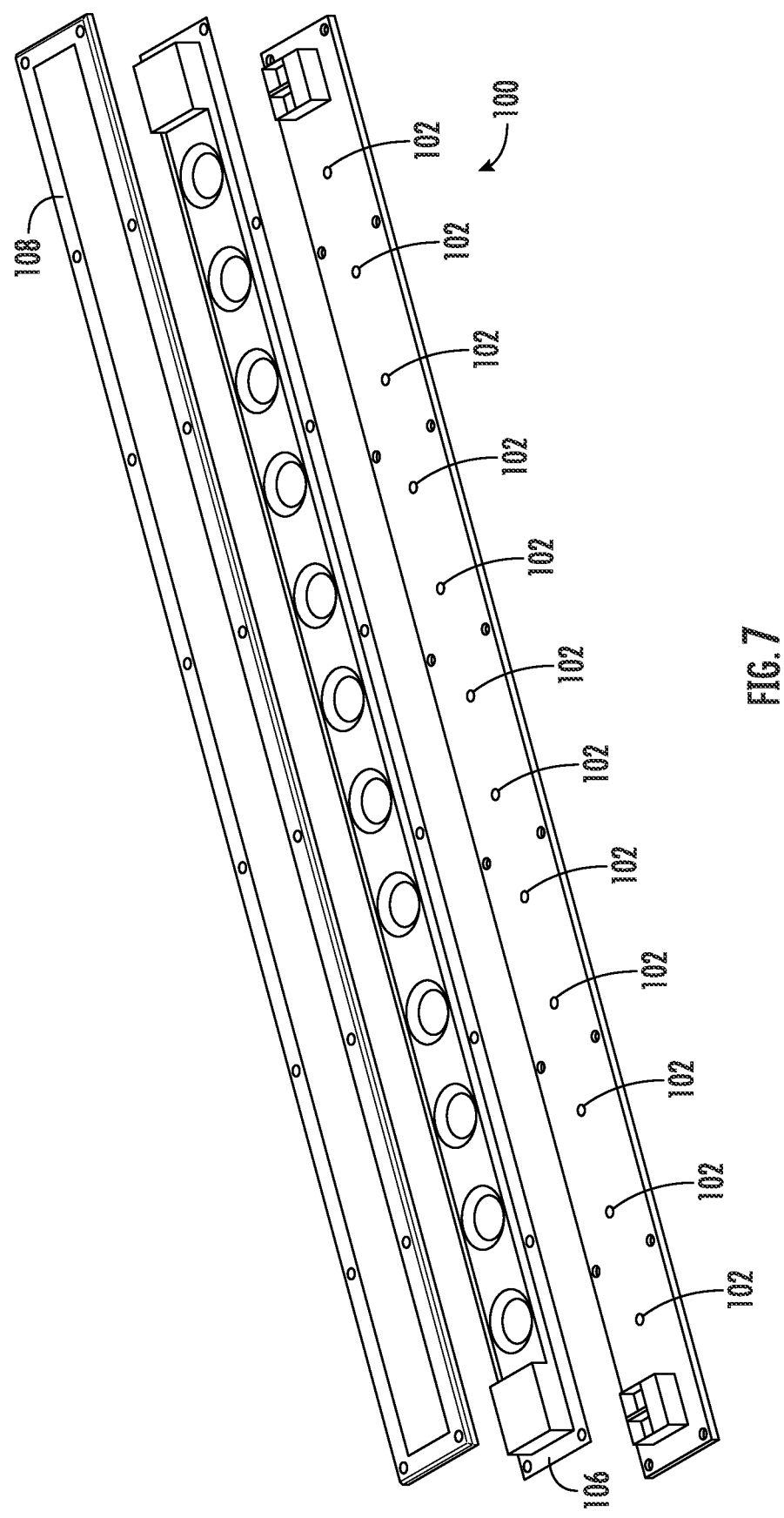
FIG. 7 provides an exploded perspective view of an exemplary sterilization light assembly of an air conditioner unit according to exemplary embodiments of the present disclosure.
Figure 8:
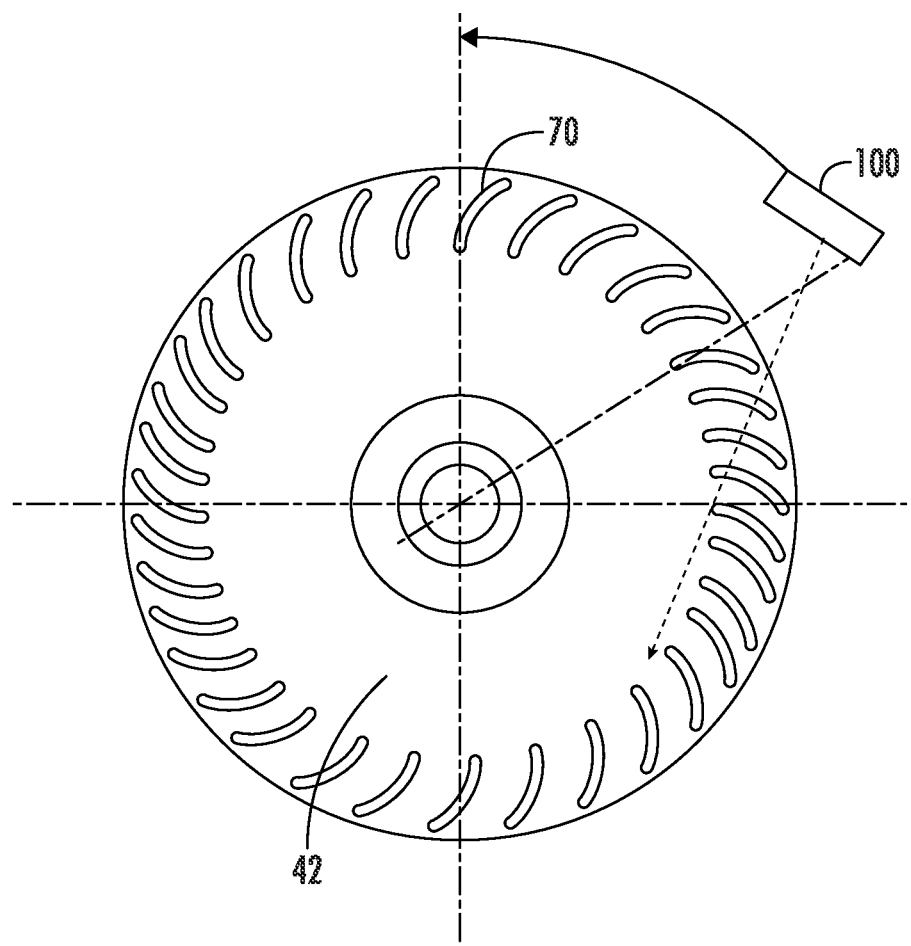
FIG. 8 provides a schematic sectional view of a portion of the exemplary air conditioner unit of FIG. 1.

Turning generally to FIGS. 1, 2, and 4, bulkhead 46 may include various peripheral surfaces that define an interior 52 thereof. For example, bulkhead 46 may include a first sidewall 54 and a second sidewall 56 which are spaced apart from each other along the lateral direction L. A rear wall 58 may extend laterally between the first sidewall 54 and second sidewall 56. The rear wall 58 may, for example, include an upper portion and a lower portion. The lower portion may have a generally linear cross-sectional shape, and may be positioned below the upper portion along the vertical direction V. Rear wall 58 may further include an indoor facing surface and an opposing outdoor facing surface. The indoor facing surface may face the interior 52 and indoor portion 12, and the outdoor facing surface may face the outdoor portion 14.

As shown, a head unit 68 may be attached to or included with housing 20 (e.g., on or adjacent to bulkhead 46, such as on the upper portion). Specifically, the head unit 68 may be positioned at or above the indoor portion 12 as part of the housing 20. In some such embodiments, the head unit 68 is further positioned above the blower fan 42. In additional or alternative embodiments, the head unit 68 extends at least from the first sidewall 54 to the second sidewall 56. Generally, the head unit 68 may define an exhaust outlet 94 having one or more openings through which air may flow (e.g., from the indoor portion 12 to the corresponding room). In some embodiments, head unit 68 further includes a cutoff panel 110 (e.g., extending below the exhaust outlet 94) to cutoff or separate portions of an airflow path 92 upstream from the blower fan 42 and downstream from the blower fan 42. Specifically, cutoff panel 110 may help direct air along an airflow path 92 of the indoor portion 12 and across the blower fan 42 before such being expelled through the exhaust outlet 94. As will be described in greater detail below, a sterilization light assembly 100 may be attached to or included with head unit 68 (e.g., on cutoff panel 110) to sterilize or otherwise reduce microbes, bacteria, or viruses within air in indoor portion 12.

In some embodiments, the upper portion of the bulkhead 46 has a generally curvilinear cross-sectional shape, and may accommodate a portion of the blower fan 42, which may be, for example, a tangential fan. Blower fan 42 may include a blade assembly 70 and a motor 72. The blade assembly 70 may include one or more metal blades (i.e., formed from a suitable metal, such as aluminum or steel, including alloys thereof) disposed about a hollow core. When assembled, the blade disposed within a fan housing 74, may be disposed at least partially within the interior 52 of the bulkhead 46, such as within the upper portion. As shown, blade assembly 70 may for example extend along the lateral direction L between the first sidewall 54 and the second sidewall 56. The motor 72 may be connected to the blade assembly 70, such as through the housing 74 to the blades via a shaft extending along a rotation axis. Operation of the motor 72 may rotate the blades or blade assembly 70 about the rotation axis, thus generally operating the blower fan 42 to motivate air through the indoor portion 12. Further, in exemplary embodiments, motor 72 may be disposed exterior to the bulkhead 46. Accordingly, the shaft may for example extend through one of the sidewalls 54, 56 to connect the motor 72 and blade assembly 70.

According to the illustrated embodiment, blower fan 42 may operate as an evaporator fan in refrigeration loop 48 to encourage the flow of air through indoor heat exchanger 40. Accordingly, blower fan 42 may be positioned downstream of indoor heat exchanger 40 along the flow direction of indoor air and downstream of heating unit 44 along the flow direction of outdoor air (e.g., when make-up air is being supplied to indoor portion 12). Optionally, blower fan 42 may be a variable speed fan and, thus, be configured to rotate at two or more preset speeds (e.g., high, medium, or low speed above 0) according to an activation signal, current, or voltage received at the blower fan 42. Additionally or alternatively, blower fan 42 may be configured to have one or more variable setpoint speeds (e.g., rotation speed). In other words, blower fan 42 a rotational speed setting (e.g., high speed) may be increased or decreased, such as by changes or instructions applied to a setpoint switch, variable resistor, or controller software.

In some such embodiments, blower fan 42 is disposed between a separate intake segment 96 and exhaust segment 98 of the airflow path 92 for indoor air through indoor portion 12. As shown, the intake segment 96 may extend from the intake openings of the room front 24 to the blower fan 42 such that the indoor heat exchanger 40 is disposed along or within the intake segment 96. The exhaust segment 98 may extend from the blower fan 42 to the exhaust outlet 94. Thus, blower fan 42 may be downstream from the intake segment 96 of the indoor portion 12 while being upstream from the exhaust outlet 94 and exhaust segment 98 of the indoor portion 12. Moreover, the cutoff panel 110 may separate or otherwise be disposed between the intake segment 96 and the exhaust segment 98.

Heating unit 44 in exemplary embodiments includes one or more heater banks 80 (e.g., disposed within the intake segment 96). Each heater bank 80 may be operated as desired to produce heat. In some embodiments, as shown, three heater banks 80 may be used. Alternatively, however, any suitable number of heater banks 80 may be used. Each heater bank 80 may further include at least one heater coil or coil pass 82, such as in exemplary embodiments two heater coils or coil passes 82. Alternatively, other suitable heating elements may be used.

The operation of air conditioner unit 10, including compressor 34 (and thus refrigeration loop 48 generally), blower fan 42, outdoor fan 32, heating unit 44, expansion device 50, and other components of refrigeration loop 48 may be controlled by a processing device such as a unit controller 84. Unit controller 84 may be in communication (via for example a suitable wired or wireless connection) to such components of the air conditioner unit 10. By way of example, the unit controller 84 may include a memory and one or more processing devices such as microprocessors, CPUs or the like, such as general or special purpose microprocessors operable to execute programming instructions or micro-control code associated with operation of unit 10. The memory may represent random access memory such as DRAM, or read only memory such as ROM or FLASH. In some embodiments, the processor executes programming instructions stored in memory (e.g., as or as part of a programmed sterilizing operation, such as method 900). The memory may be a separate component from the processor or may be included onboard within the processor.

Unit 10 may additionally include a control panel 86 and one or more user inputs 88, which may be included in control panel 86. The user inputs 88 may be in communication with the unit controller 84. A user of the unit 10 may interact with the user inputs 88 to operate the unit 10, and user commands may be transmitted between the user inputs 88 and unit controller 84 to facilitate operation of the unit 10 based on such user commands. A display 90 may additionally be provided in the control panel 86, and may be in communication with the unit controller 84. Display 90 may, for example be a touchscreen or other text-readable display screen, or alternatively may simply be a light that can be activated and deactivated as required to provide an indication of, for example, an event or setting for the unit 10.

Referring especially to FIGS. 3 through 8, greater detail of unit 10 is provided, in particular regarding sterilization light assembly 100. Generally, sterilization light assembly 100 is disposed or mountable within the indoor portion 12 (e.g., at the intake segment 96) to transmit an ultraviolet light emission to air residing or flowing through indoor portion 12. To this end, sterilization light assembly 100 includes one or more ultraviolet (UV) light sources 102 (e.g., light emitting diodes or LEDs) configured to emit radiation in the germicidal wavelength range of 100 to 300 nanometers. Optionally, one or more light sources 102 may be ultraviolet C (UVC) light sources 102 configured to emit radiation between 200 to 280 nanometers or 245 to 265 nanometers. Additionally or alternatively, one or more light sources 102 may be configured as a variable-intensity light source. In other words, the intensity (e.g., radiosity as measured in $\mu W/cm^2$) of the emitted UVC light (i.e., UVC light emissions) from one or more light sources 102 may be selectively changed (i.e., increased or decreased). Such changes may be made, for instance, by an assembly controller 120 of sterilization light assembly 100 based on one or more criteria (e.g., a detected condition, user preference, etc.).

Although described below in an installed position disposed within indoor portion 12, one or more portions of sterilization light assembly 100 may be selectively removed or held apart from housing 20 (e.g., prior to installation). Thus, sterilization light assembly 100 may be provided as (or as part of) an aftermarket kit to be installed in a previously assembled air conditioner unit. When installed, sterilization light assembly 100 may further be connected to a power source (e.g., directly or through a selective electrical connection with unit controller 84), such as a municipal (e.g., AC) power grid or a self-contained (e.g., DC) battery cell.

In some embodiments, sterilization light assembly 100 is disposed along the airflow path 92. Sterilization light assembly 100 may, in turn, be installed in fluid communication with blower fan 42. Optionally, sterilization light assembly 100 may be directed at blower fan 42. During use, light emissions from sterilization light assembly 100 may be projected or guided to the blower fan 42. In some such embodiments, sterilization light assembly 100 is directed perpendicular to the rotation axis A (e.g., perpendicular to the lateral direction L). At least a portion of the UV light emissions from sterilization light assembly 100 may thus be projected or guided between the center (e.g., hollow center) and outer periphery of the diameter of blower fan 42 (e.g., defined at the radial extremes of blade assembly 70). Thus, sterilization light assembly 100 may be projected at an offset angle or otherwise off center relative to the rotation axis A. Advantageously, transmission of UV light through individual fan blades (e.g., to a region below the fan blades) may be limited while ensuring transmission of UV light to the fan blades of blade assembly 70.

As shown, sterilization light assembly 100 may be disposed upstream from blower fan 42 within the intake segment 96. Alternatively, sterilization light assembly 100 may be disposed downstream from blower fan within exhaust segment 98. During use, air motivated by blower fan 42 may thus be subjected to UV light emissions or radiation, thereby advantageously reducing or eliminating active microbes, bacteria, or viruses within the air. Optionally, at least a portion of the air within blower fan 42 may be subjected to the UV light as the UV light passes through gaps between the blades in the rotating blade assembly 70. Notably, the metal blades of blade assembly 70 may be able to endure exposure to UV light emissions without breaking down or becoming brittle.

As noted above, head unit 68 may define air exhaust outlet 94. Specifically, air exhaust outlet 94 may be defined above at least a portion of blower fan 42 along the vertical direction V or forward from blower fan 42 along the transverse direction T. Cutoff panel 110 may, thus, extend along the transverse direction T while separating or being disposed between the intake segment 96 and the exhaust segment 98 along the vertical direction V. In some such embodiments, sterilization light assembly 100 is disposed beneath exhaust outlet 94 along the vertical direction V. For instance, sterilization light assembly 100 may be attached to the cutoff panel 110, such as by a mounting bracket 104 that holds sterilization light assembly 100 and is joined to cutoff panel 110 (e.g., via a suitable mechanical fastener, adhesive, etc.).

In the illustrated embodiments, sterilization light assembly 100 is disposed directly beneath cutoff panel 110. Optionally, sterilization light assembly 100 may be held above a bottom half or hemisphere of blower fan 42 (i.e., at a higher height than the half of blower fan 42 below a horizontal plane extending from the rotation axis A). Moreover, cutoff panel 110 (and thus sterilization light assembly 100) may also be disposed below (i.e., at a lower height) than a top end of blower fan 42. A lower restrictor wall (e.g., formed by heating unit 44 or heater banks 80) may be disposed below blower fan 42 within intake segment 96 and forward therefrom, while the rest of the airflow path 92 between the lower wall and cutoff panel 110 is generally unobstructed. Thus, intake segment 96 may restrict or funnel air therealong to 30 to 40% of the front circumference of blower fan 42. Advantageously, a significant portion of air flowing to blower fan 42 through intake segment 96 may thus be subjected to emissions or radiation from sterilization light assembly 100 (e.g., while preventing such emissions from being visible to a user in front or above the unit 10).

As described, sterilization light assembly 100 may be disposed upstream from blower fan 42. For instance, sterilization light assembly 100 may be disposed between indoor heat exchanger 40 and blower fan 42 along the transverse direction T. Additionally or alternatively, mounting bracket 104 supporting the sterilization light assembly 100 within the indoor portion 12 may be formed from or include a metal material (e.g., aluminum or steel, including alloys thereof). When assembled, mounting bracket 104 may have a back face opposite of the sterilization light assembly 100 and generally facing the upstream portion of intake segment 96. Thus, air drawn along the intake segment 96 may contact the back face of mounting bracket 104. Notably, air drawn along the airpath to blower fan 42 may aid in cooling sterilization light assembly 100. For instance, heat may be conducted through mounting bracket 104 and to the air through flowing through intake segment 96.

In certain embodiments, one or more UV light sources 102 of sterilization light assembly 100 are advantageously covered or sealed (e.g., to prevent the passage of moisture thereto, which might otherwise be significant or problematic after accumulating on indoor heat exchanger 40). For instance, a lens casing 106 (e.g., UV-transparent lens casing) may seal at least one light source 102 (e.g., and a control board thereof) against mounting bracket 104. Optionally, a peripheral bracket 108 may extend about a rim of the lens casing 106 to sandwich the rim against mounting bracket 104 and, thus, hold lens casing 106 to mounting bracket 104. Although most solid materials absorb significant portions of UV light, lens casing 106 may be formed from a UV-permissive polymer (e.g., configured to absorb less than 60% of UV emissions from sterilization light assembly 100). When assembled, at least a portion of lens casing 106 may be disposed between light source 102 and blower fan 42 (e.g., along the transverse direction T).

Along with being installed on or within indoor portion 12, sterilization light assembly 100 may be installed in operable communication (e.g., direct or indirect electrical communication) with one or more other components of unit 10. In particular, an onboard or assembly controller 120 (e.g., microprocessor, memory, or switch, which may be mounted on mounting bracket 104) of sterilization light assembly 100 may operably communicate with blower fan 42. To that end, a fan monitor 122 may be connected (e.g., electrically connected) to sterilization light assembly 100 to detect one or more signals (e.g., data signals or electrical power currents) communicated to blower fan 42 (e.g., from unit controller 84). As shown, fan monitor 122 may generally be disposed on an electrical path 124 (e.g., wire, harness, bus, etc.) to blower fan 42 from a power source or unit controller 84. Thus, fan monitor 122 may be disposed in communication between blower fan 42 and unit controller 84. Fan monitor 122 itself may include any suitable element for drawing, diverting, or detecting an electrical current (e.g., including an electrical or magnetic field generated by the same) through the electrical path 124, as will be described in greater detail below In some embodiments, fan monitor 122 directly connects to the electrical path 124. As an example, fan monitor 122 may include an electrical circuit connected to assembly controller 120. In other words, fan monitor 122 may connect electrical path 124 to sterilization light assembly 100. Such a connection may be facilitated by a dongle enclosure (e.g., within which fan monitor 122 is enclosed) that is directly connected to unit controller 84 and (directly or indirectly) connected to sterilization light assembly 100 and blower fan 42 (e.g., via separate electrical wires or sub-paths). In some such embodiments, fan monitor 122 may serve to pass one or more fan signals between unit controller 84 and blower fan 42 (e.g., without significant modification of the same) to detect or measure such signals. Optionally, the fan signals may be further used to power sterilization light assembly 100 (e.g., activate the UVC light source 102). For instance, a portion of the current of one or more fan signals may be received at the sterilization light assembly 100, which may draw power from the same. Alternatively, sterilization light assembly 100 may be powered via a current from a separate line or power source (e.g., an AC power grid, DC battery cell, etc.) connected to the sterilization light assembly 100. For instance, fan monitor 122 may include a current-controlled relay configured to selectively permit electrical communication between the separate power source and the sterilization light assembly 100. Specifically, the current-controlled relay may be activated in response to a current through electrical path 124 to close an electrical line or path from the separate power source to the sterilization light assembly 100, thereby permitting sterilization light assembly 100 to activate (e.g., transmit one or more UV light emissions from the UVC light source 102).

In additional or alternative embodiments, fan monitor 122 indirectly connects to the electrical path 124. As an example, fan monitor 122 may include or be provided as a current sensor (e.g., CT sensor/current transformer, Rogowski sensor, Hall-effect sensor, giant magneto-resistive (GMR) sensor, etc.) disposed on or around the electrical path 124. In other words, the current sensor or fan monitor 122 may be mounted in close proximity to the wires or conductive elements defining electrical path 124 to detect an electrical current. Fan monitor 122 may further connect (e.g., electrically connect) to sterilization light assembly 100. A current transmitted through electrical path 124 (e.g., to blower fan 42), may thus be detected at the current sensor to generate a separate detection signal, which can be transmitted to and received power sterilization light assembly 100. In response to such detection signals, sterilization light assembly 100 may then be activated (e.g., transmit one or more UV light emissions from the UVC light source 102).

Figure 9:
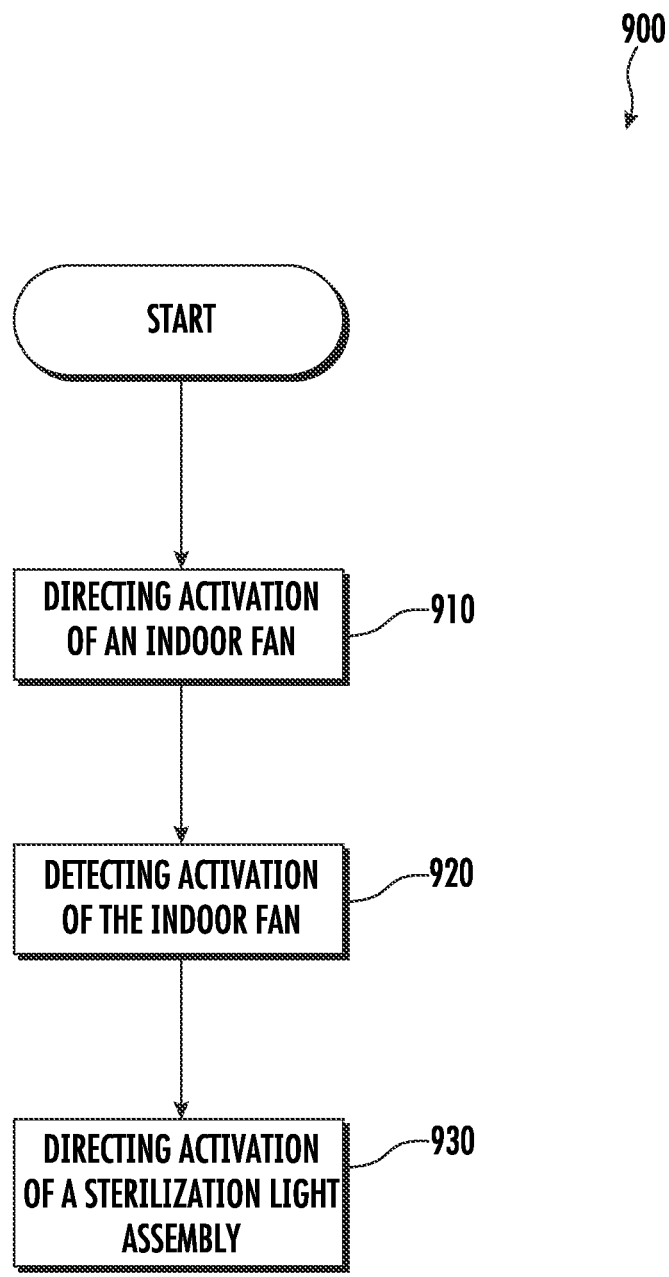
FIG. 9 provides a flow chart illustrating a method of operating an air conditioner unit according to exemplary embodiments of the present disclosure.

Turning now to FIG. 9, the present disclosure may further be directed to methods (e.g., method 900) of operating an air-treatment appliance or unit, such as air conditioner unit 10. In exemplary embodiments, the assembly controller 120 or unit controller 84 (e.g., separately or together as a general "controller") may be operable to perform various steps of a method in accordance with the present disclosure (e.g., as part of a sterilizing operation).

The method 900 may occur as, or as part of, a sterilizing operation (e.g., initiated or performed, at least in part, during a cooling or heating operation) of the air conditioner unit 10. In particular, the methods disclosed herein may advantageously permit a user to automatically sterilize air through air conditioner unit 10 using an after-market kit (e.g., including sterilization light assembly or fan monitor) installed into unit 10 subsequent to assembly and purchase of unit 10 generally. Additionally or alternatively, the methods disclosed herein may advantageously permit a user to reliably sterilize air without the need of complex programming dedicated to sterilization (e.g., within unit controller 84).

At 910, the method 900 includes directing activation of the indoor fan. Specifically, the indoor fan (i.e., blower fan) may be activated to rotate and thereby motivate air through the indoor portion. In some embodiments, 910 includes transmitting one or more activation signals (e.g., data signals or electrical power currents) to the indoor fan. Such activation signals may be transmitted, for instance, by the unit controller or power source of the air conditioner unit as part of a programmed air-treatment (e.g., cooling, heating, dehumidifying, etc.) cycle, as would be understood. Moreover, 910 may generally indicate an intent by the unit to rotate the indoor fan and thereby motivate air through the unit (e.g., at the indoor portion). Indoor fan may be provided as a variable speed fan. As would be understood, the activation signals may thus be selectively varied (e.g., increased or decreased), such as to vary the rotation speed of the indoor fan. As an example, the current or voltage to the indoor fan may be varied to change the rotation speed of the indoor fan (e.g., between a high, medium, or low speed above 0). As an additional or alternative example, one or more discrete speed setpoints (e.g., high speed, medium speed, or low speed) may be varied or changed based on a received setpoint signal. Thus, the speed setpoint for a relatively high speed may be changed, the speed setpoint for a relatively medium speed may be changed, or the speed setpoint for a relatively low speed may be changed (e.g., via instructions or variations in an activation signal).

At 920, the method 900 includes detecting activation of the indoor fan to motivate air through the indoor portion. Thus, in addition to merely transmitting an activation signal (e.g., at 910), the method 900 includes separately detecting or confirming the transmission of the activation signal. In turn, it may be confirmed (e.g., at the assembly controller) that the indoor fan is being commanded to actually rotate.

As described above, a fan monitor may be provided to detect one or more signals (e.g., data signals or electrical power currents) communicated to the indoor fan. In some such embodiments, 920 includes monitoring a current (i.e., electrical power current) to the indoor fan. The current may be monitored directly or indirectly. Thus, in certain embodiments, 920 (e.g., monitoring the current) includes sensing the current from a current sensor disposed on the electrical path to the indoor fan, such as for indirect monitoring. In either direct or indirect monitoring, 910 may include detecting not only the presence of the current, but one or more attributes (e.g., strength) of the current. Specifically, the absolute or relative magnitude of activation signal 920 may be detected (e.g., above a nominal level to indicate the relative rotation speed of the indoor fan). As an example, increases in rotation speed of the indoor fan may be directed by increases in the current value or voltage value monitored by the fan monitor. Thus, variations in the directed rotation speed of the indoor fan may be detected at 920 (e.g., on the assembly controller). Optionally, 920 may include measuring one or more attributes thereof. For instance, a current value (e.g., in Amperes) or voltage value (e.g., in volts) may be measured from the current.

At 930, the method 900 includes directing activation of the sterilization light assembly to transmit an ultraviolet light emission within the indoor portion based on detected activation of the indoor fan. In turn, activation of the sterilization light assembly may prompt (e.g., cause or instruct) activation of the sterilization light assembly such that the one or more light sources are able to transmit ultraviolet light emissions. For instance, 930 may include directing the UVC light source to transmit the ultraviolet light emission between 200 to 280 nanometers within the airflow path.

As noted above, one or more of the UVC light sources may be a variable-intensity light source. Thus, the intensity (e.g., radiosity) of the transmitted ultraviolet light emissions may be a variable intensity value (e.g., as measured in $\mu W/cm^2$). In certain embodiments, the intensity (i.e., variable intensity value) can be varied based on the variable rotation speed of the indoor fan. Increases in fan speed (e.g., detected at 920) may prompt increases the intensity of the ultraviolet light emissions. Decreases in fan speed (e.g., detected at 920) may prompt decreases in the intensity of the ultraviolet light emissions. Optionally, the variable intensity value is proportional to the variable rotation speed. Additionally or alternatively, the variable intensity value may be proportional to the monitored current. Thus, as the current to the indoor fan is varied, the intensity of one or more of the UVC light sources may be similarly or proportionally varied.

As noted above, the sterilization light assembly may draw power from the same current as is monitored at the fan monitor. In such embodiments, the monitored current may thus simultaneously power the indoor fan and the sterilization light assembly. In alternative embodiments, though, a separate connection or current (e.g., from a power source) powers the sterilization light assembly apart from the indoor fan.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. An air conditioner unit for conditioning an indoor space, the air conditioner unit comprising:
   a housing defining an indoor portion and an outdoor portion, the housing further defining an exhaust outlet downstream from the indoor portion to exhaust air therefrom;
   an outdoor heat exchanger assembly disposed in the outdoor portion and comprising an outdoor heat exchanger;
   an indoor heat exchanger assembly disposed in the indoor portion and comprising an indoor heat exchanger and an indoor fan;
   a compressor in fluid communication with the outdoor heat exchanger and the indoor heat exchanger to circulate a refrigerant between the outdoor heat exchanger and the indoor heat exchanger;
   a sterilization light assembly disposed within the indoor portion; and
   a controller in operable communication with the indoor fan and the sterilization light assembly, the controller being configured to initiate a sterilizing operation comprising
      directing activation of the indoor fan to motivate air through the indoor portion,
      detecting activation of the indoor fan to motivate air through the indoor portion, and
      directing activation of the sterilization light assembly to transmit an ultraviolet light emission within the indoor portion based on detected activation of the indoor fan,
      wherein detecting activation of the indoor fan comprises monitoring a current to the indoor fan, the monitored current simultaneously powering the indoor fan and the sterilization light assembly such that the indoor fan is activated to rotate together with the transmitted ultraviolet light emission from the sterilization light assembly.

2. The air conditioner unit of claim 1, wherein intensity of the transmitted ultraviolet light emission is a variable intensity value based on a variable rotation speed of the indoor fan.

3. The air conditioner unit of claim 2, wherein the variable intensity value is proportional to the variable rotation speed.

4. The air conditioner unit of claim 1, wherein detecting activation of the indoor fan comprises sensing the current from a current sensor disposed on an electrical path to the indoor fan.

5. The air conditioner unit of claim 1, further comprising a metal mounting bracket supporting the sterilization light assembly within the indoor portion along an airflow path between an intake segment of the indoor portion and an exhaust segment of the indoor portion upstream from the exhaust outlet,
   wherein the indoor fan is disposed along the airflow path,
   wherein the sterilization light assembly comprises an ultraviolet C (UVC) light source and lens casing sealing the UVC light source against the metal mounting bracket to prevent moisture from contacting the UVC light source, and
   wherein directing activation of the sterilization light assembly comprises directing the UVC light source to transmit the ultraviolet light emissions between 200 to 280 nanometers within the airflow path.

6. The air conditioner unit of claim 1, wherein intensity of the transmitted ultraviolet light emission is a variable intensity value based on the monitored current.

7. The air conditioner unit of claim 6, wherein the variable intensity value is proportional to the monitored current.

8. An air conditioner unit for conditioning an indoor space, the air conditioner unit comprising:
   a housing defining an indoor portion and an outdoor portion, the housing further defining an exhaust outlet downstream from the indoor portion to exhaust air therefrom;
   an outdoor heat exchanger assembly disposed in the outdoor portion and comprising an outdoor heat exchanger;
   an indoor heat exchanger assembly disposed in the indoor portion and comprising an indoor heat exchanger and an indoor fan;
   a compressor in fluid communication with the outdoor heat exchanger and the indoor heat exchanger to circulate a refrigerant between the outdoor heat exchanger and the indoor heat exchanger;
   a sterilization light assembly disposed within the indoor portion and directed at the indoor fan above a bottom half of the indoor fan, the sterilization light assembly being electrically connected to the indoor fan; and
   a controller in operable communication with the indoor fan and the sterilization light assembly, the controller being configured to initiate a sterilizing operation comprising
   directing activation of the indoor fan to motivate air through the indoor portion,
   detecting activation of the indoor fan to motivate air through the indoor portion, and
   directing activation of the sterilization light assembly to transmit an ultraviolet light emission within the indoor portion based on detected activation of the indoor fan,
   wherein detecting activation of the indoor fan comprises monitoring a current to the indoor fan, the monitored current simultaneously powering the indoor fan and the sterilization light assembly such that the indoor fan is activated to rotate together with the transmitted ultraviolet light emission from the sterilization light assembly.

9. The air conditioner unit of claim 8, wherein intensity of the transmitted ultraviolet light emission is a variable intensity value based on a variable rotation speed of the indoor fan, wherein the variable intensity value is proportional to the variable rotation speed.

10. The air conditioner unit of claim 8, wherein detecting activation of the indoor fan comprises sensing the current from a current sensor disposed on an electrical path to the indoor fan.

11. The air conditioner unit of claim 10, further comprising a metal mounting bracket supporting the sterilization light assembly within the indoor portion along an airflow path between an intake segment of the indoor portion and an exhaust segment of the indoor portion upstream from the exhaust outlet,
   wherein the indoor fan is disposed along the airflow path,
   wherein the sterilization light assembly comprises an ultraviolet C (UVC) light source and lens casing sealing the UVC light source against the metal mounting bracket to prevent moisture from contacting the UVC light source, and
   wherein directing activation of the sterilization light assembly comprises directing the UVC light source to transmit the ultraviolet light emissions between 200 to 280 nanometers within the airflow path.

12. The air conditioner unit of claim 10, wherein intensity of the transmitted ultraviolet light emission is a variable intensity value based on the monitored current.

13. The air conditioner unit of claim 12, wherein the variable intensity value is proportional to the monitored current.

* * * * *